United States Patent [19]
Limousin et al.

[11] Patent Number: 5,584,867
[45] Date of Patent: Dec. 17, 1996

[54] METHOD AND APPARATUS FOR CONTROLLING A DOUBLE ATRIAL TRIPLE CHAMBER CARDIAC PACEMAKER HAVING A FALLBACK MODE

[75] Inventors: Marcel Limousin, Montrouge; Martine Remy, Jouy en Josas, both of France

[73] Assignee: ELA Medical S.A., Montrouge, France

[21] Appl. No.: 416,306

[22] Filed: Apr. 4, 1995

[30] Foreign Application Priority Data

Apr. 5, 1994 [FR] France .................................. 94 03987

[51] Int. Cl.⁶ .............................................. A61N 1/368
[52] U.S. Cl. ................................. 607/9; 607/4; 607/14; 607/15
[58] Field of Search ........................... 607/4, 9, 14, 15, 607/123

[56] References Cited

U.S. PATENT DOCUMENTS

| | | | |
|---|---|---|---|
| 4,932,406 | 6/1990 | Berkovits | 128/419 |
| 5,107,850 | 4/1992 | Olive | 128/705 |
| 5,226,415 | 7/1993 | Girodo et al. | |

FOREIGN PATENT DOCUMENTS

| | | | |
|---|---|---|---|
| 2544989 | 4/1983 | France | A61N 1/36 |
| WO92/09331 | 6/1992 | WIPO | A61N 1/368 |
| WO92/14511 | 9/1992 | WIPO | A61N 1/368 |

*Primary Examiner*—Marvin M. Lateef
*Assistant Examiner*—Shawna J. Shaw
*Attorney, Agent, or Firm*—Orrick, Herrington & Sutcliffe

[57] ABSTRACT

Control of a double atrial triple chamber cardiac pacemaker having a programmable fallback mode. The triple chamber pacemaker has a right atrial electrode and a left atrial electrode connected to the same atrial detection/stimulation circuit, as well as a ventricular electrode connected to a ventricular detection/stimulation circuit of the pacemaker. The fallback mode involves desynchronization of the ventricular stimulation from the detected atrial rhythm when the atrial rhythm is too rapid. The pacemaker also includes a fallup mode of pacing in which there is a progressive re-synchronization of ventricular stimulation to the atrial rhythm when the atrial rhythm falls to a less rapid rhythm. The triple chamber pacemaker senses a succession of signals at the atrial circuit, and in response to each detection of a signal, defines a masking period of inter-atrial propagation for not sensing signals at the atrial circuit, measures an interval of time separating two successive sensed signals, compares the measured time interval to a predetermined control value, and triggers the fallup mode of progressive re-synchronization when the measured time interval becomes greater than the control value.

6 Claims, 1 Drawing Sheet

METHOD AND APPARATUS FOR CONTROLLING A DOUBLE ATRIAL TRIPLE CHAMBER CARDIAC PACEMAKER HAVING A FALLBACK MODE

FIELD OF THE INVENTION

The present invention concerns a "triple chamber" cardiac pacemaker, more specifically, a dual chamber pacemaker capable of sensing and stimulating the right ventricle and the right and left atria. The present invention more particularly concerns such a double atrial triple chamber cardiac pacemaker possessing a "fallback" mode of functioning, in which there is a desynchronization of the ventricular stimulation to atrial activity when the atrial rhythm is too rapid, and a "fallup" mode of functioning in which there is a progressive re-synchronization of ventricular stimulation to atrial activity when the atrial rhythm becomes less rapid and is physiologically tolerable to the patient.

BACKGROUND OF THE INVENTION

If a patient develops an atrial tachycardia crisis (also called "supra-ventricular tachycardia" or SVT), it is necessary to limit the ventricular synchronization to a given range. This is necessary to avoid too rapid a stimulation of the ventricle, which would be beyond a maximal frequency that is physiologically tolerable by the individual, the so-called "maximal frequency of ventricular stimulation" or "maximal synchronization frequency".

To achieve this goal, the cardiac pacemaker is provided with a fallback mode of functioning in which it tries to keep a certain synchronization beyond the maximal synchronization frequency (i.e., operation in a Wenkebach operating mode for determined time interval or number of cardiac cycles) and, if the atrial frequency continues to exceed the maximal synchronization frequency, it changes to an asynchronous mode of ventricular stimulation. In the asynchronous mode the ventricular stimulation frequency is typically reduced to a frequency that is lower than the maximal synchronization frequency.

As soon as the atrial frequency falls below the maximal synchronization frequency limit, a phase of progressive re-synchronization also known as "fallup" is started.

FR-A-2,544,989 and U.S. Pat. No. 5,226,415 describe such modes of functioning, applied in the case of a "double chamber" type pacemaker. Such a fallback and fallup mode of operating also are implemented in the commercial devices known as the models CHORUS, CHORUS II and CHORUS RM double chamber pulse generators, available from ELA Medical, Montrouge, France.

The present invention is directed to the particular case where such a fallback mode is incorporated in a cardiac pacemaker of the "triple chamber" type. As noted, triple chamber type pacemakers include, in addition to a ventricular electrode (generally a bipolar endocardial lead), two atrial electrodes with one atrial probe implanted on each of the two atria and with both atrial electrodes connected to a corresponding single input to the pacemaker by use of a Y connector.

The atrial electrode is thus a double electrode but, in contrast with a classic "bipolar" electrode having two electrodes where the distal and proximal terminals are distanced only a few millimeters, the two terminals of the double atrial electrode are relatively spaced further apart, for example, a typical distance on the order of 5 cm. The double atrial electrode is preferably two unipolar electrodes connected by a Y-connector.

Some pacemakers, e.g., the model CHORUS II devices, also are equipped with an ability to switch between operation a bipolar mode of detection and stimulation, and a monopolar (unipolar) mode of detection and stimulation. These modes are well known to persons of ordinary skill in the art, and such a switching can be typically realized by external programming. Further, the switching can apply individually to the atrial circuit as well as to the ventricular circuit of a double chamber pacemaker. Thus, a triple chamber pacemaker can be constructed of a double chamber pacemaker and the double atrial electrode.

The triple chamber cardiac pacemaker has been used in a relatively satisfactory manner for some years. They are useful in connection with patients having indications presenting an "inter-atrial block" sinusal disorder, in which there is a deficient signal propagation (insufficient or too long) from the right atrium to the left atrium.

Thus, if only one atria is stimulated (e.g., the right atrium, as occurs in the classic situation of the "double chamber" pacemaker), the other atrium (e.g., the left atrium), which is not stimulated, would receive the depolarization wave coming from the stimulated atrium, if at all, after an excessively long period. Sometimes the period is longer than the atrial-ventricular (AV) delay. Such a phenomenon can result in a stimulated contraction of ventricles occurring before draining of the left atrium, and therefore before the mitral valve has closed. This produces a counter-flow of blood from the ventricle to the left atrium and a diminution of the hemodynamic efficiency.

In addition, the electrical desynchronization of the two atria favors the appearance of tachyarrhythmia events.

Further, it has been recognized that the inter-atrial propagation delay period increases with the patient's effort. Therefore, an increase of the physiological activity of the patient apparently favors the risk of appearance of tachyarrhythmia and/or reduced hemodynamic efficiency.

The known "triple chamber" pacemakers operate by stimulating both the left and right atria simultaneously. This is done to avoid the appearance or the persistence of the cited drawbacks. Nevertheless, clinical studies have revealed a sometimes defective functioning of the fallback mode for some patients, with a period of desynchronization continuing even after the return of the atrial rhythm to below the maximal synchronization limit. Such disfunction, whose origin had not up until now been recognized to exist or understood, could even continue for so long that the fallback mode is de-activated. Consequently, the therapist is obliged to choose between a functioning of the type "triple chamber without fallback" or of the type "double chamber with fallback", and therefore, not be able to combine, with all necessary security guarantees, a functioning of the triple chamber stimulation with a fallback mode.

OBJECT AND SUMMARY OF THE INVENTION

It is, therefore, an object of the present invention to propose an improved process to control a "triple chamber" cardiac pacemaker allowing it to activate a fallback mode by minimizing risk of disfunctioning, thereby to benefit both from the advantages of the triple chamber stimulation mode and the possibility of functioning in a fallback mode in case of an excessive atrial rhythm, notably in case of crisis of atrial tachycardia and SVT.

The present invention is essentially based on the discovery by the inventors of a probable cause of the disfunctioning associated with the triple chamber pacemakers operating in a fallback mode. More particularly, as is explained in more detail below, the inventors have recognized that the fallback mode disfunction is very probably the consequence of an intervening confusion, in some situations, of the origin of atrial signals sensed by the atrial detection circuits of the pacemaker. In this regard, the triple chamber pacemaker receives (senses) on a single input two successive and different signals corresponding, first, to the depolarization wave front stemming from the right atrium sensed by the electrode terminal placed on the right atrium and, second, to the same depolarization wave front sensed by the electrode terminal placed on the left atrium, therefore with a delay corresponding to the time of inter-atrial propagation period.

In some situations, notably if the inter-atrial propagation time is significant, these two signals can appear in the form of a wave doublet, namely two distinct signals. The atrial detection circuit of the pacemaker can, in some cases, wrongly interpret this wave doublet as two successive depolarization waves corresponding to two successive atrial events and, considering their rapid succession, misinterpret the doublet to correspond to a very rapid atrial rhythm. Consequently, the pacemaker logic will place or maintain the pacemaker in the fallback mode, although the real atrial rhythm may be or have already descended below the maximal synchronization frequency limit to permit the start of the progressive re-synchronization (fallup). If the misinterpretation continues for some time interval, then the pacemaker logic, when suitably programmed, will revert to pacing in the asynchronous mode and no longer use the fallback mode.

It is then another object of the invention to provide an appropriate discrimination allowing the pacemaker to avoid confusing a wave doublet coming from the same atrial depolarization wave front with consecutive atrial depolarization signals, and to avoid thus the persistence of the fallback mode, and a specific disfunctioning of the triple chamber stimulation, whose origin was until now unknown and hence uncorrectable by the pacemaker.

The invention is thus applicable to control a typical double atrial triple chamber cardiac pacemaker, having a right atrial electrode and a left atrial electrode commonly connected to one and the same circuit for the detection of spontaneous atrial events and stimulation of the atrium, as well as a ventricular electrode connected to a ventricular circuit of detection of spontaneous atrial events and stimulation of the ventrical. The pacemaker includes operation in a fallback mode in which the ventricular stimulation is desynchronized from the atrial rhythm when the atrial rhythm is too rapid, and operation in a fallup mode of a progressive resynchronization of the ventricular stimulation to return to synchrony with the atrial rhythm when the atrial rhythm is less rapid, namely below a maximal synchronization frequency level.

One aspect of the invention is directed to a control process for use in a fallback operating mode characterized by steps of:

receiving (detecting) at the input of the atrial circuit a succession of signals;

in response to each detection of a signal, establishing a masking period corresponding to the inter-atrial propagation period;

applying the masking period and measuring an interval of time separating two successive signals, the first signal triggering the masking period and the second signal being detected subsequent to the end of the masking period;

comparing the measured interval of time to a predetermined control value; and initiating a fallup mode of progressive resynchronization when the measured time interval becomes greater than the predetermined control value.

In a first embodiment, the process step of establishing the inter-atrial propagation period is implemented by starting a specific refractory period in response to the first sensed atrial event. The refractory period is used as a mask for the sensed signals of a doublet, to mask the detection of the second coming wave signal following detection of the first appearing wavefront during the refractory period. Thus, if a second wave signal is not sensed during the refractory period, the next sensed depolarization wave will be from a following atrial event, and not a second wave of a doublet from the same atrial event. In other words, if the second sensed wave is after the refractory period, the two successive detections are not a doublet but rather are two beats of a fast atrial rhythm.

In a second embodiment, the process step of establishing the inter-atrial propagation period is implemented by switching the atrial signal detection mode from a bipolar mode to a monopolar mode. Preferably, in this second embodiment, after the step of initiating the progressive resynchronization mode, the step of switching further switches the atrial signal detection from a monopolar mode to a bipolar mode.

Another aspect of the invention concerns apparatus for controlling the pacemaker which includes logic circuits configured and operable to perform the aforementioned control process. Such apparatus logic circuits may be a microprocessor executing a software program stored in a memory device and signal conditioning (and digital conversion) circuits for sensing depolarization signals and processing the sensed signals in the manner described, or discrete logic circuits including latches, counters, flipflops, comparators and gates configured for performing the same functions, albeit in a different way.

BRIEF DESCRIPTION OF THE DRAWINGS

Others characteristics and advantages of the invention will appear to a person of ordinary skill in the art in view of the following detailed description of a preferred embodiment of the present invention, made with reference to drawings annexed, in which.

DETAILED DESCRIPTION OF THE DRAWINGS

Figure 1:
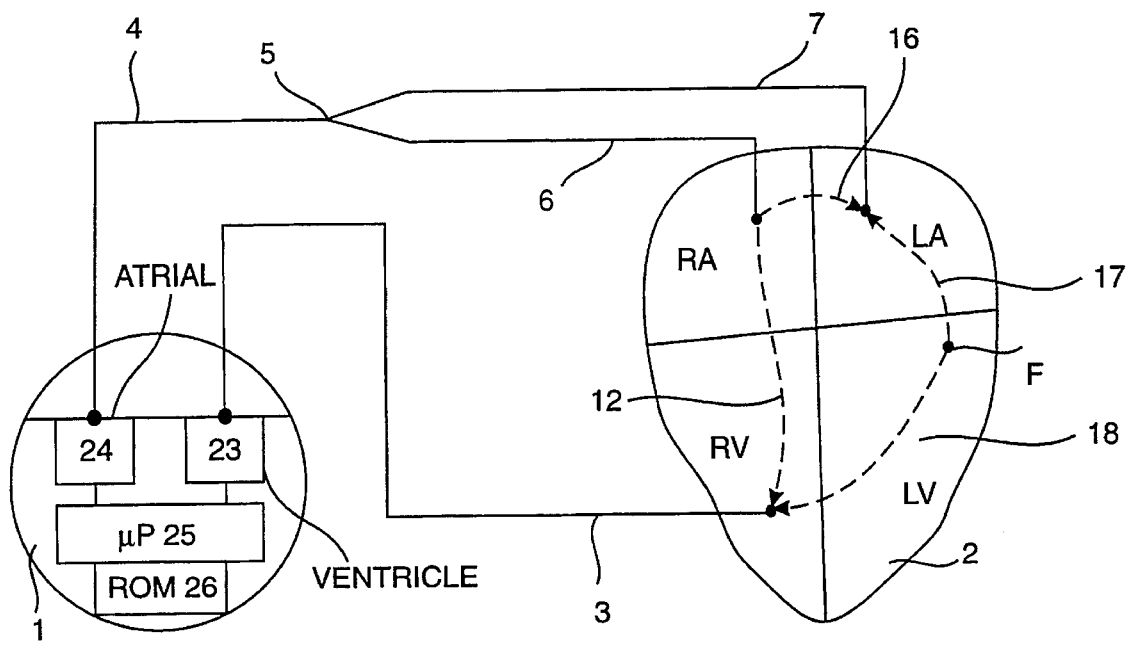
FIG. 1 is a schematic view of the connection of a double atrial triple chamber pacemaker and the implantation of the atrial and ventricular endocardial electrodes on the myocardia (muscle) of the different cardiac chambers.

With reference to FIG. 1, the reference 1 designates a cardiac pacemaker, that is a typical DDD or DDT type device. Pacemaker 1 is a double bipolar pacemaker, in which there is both atrial and ventricular signal detection and ventricular and atrial stimulation, functioning in triggered mode. A triggered mode refers to producing a stimulation from the sensing of a signal on the corresponding electrode or, in an imposed manner, in the absence of a sensed signal after a given predetermined time.

The pacemaker 1 is connected to the myocardia 2 by a configuration of the triple chamber type, that is to say with a ventricular electrode 3 connected to the right ventricle RV and a double atrial electrode 4 connected to each of the two atria, the right atrium RA and the left atrium LA, by the intermediary of a Y connector 5, and two respective electrode conductors (terminals) 6 and 7. As a result of Y connector 5, an atrial circuit 24 of detection/stimulation of the pacemaker 1 is connected to the electrode 4 at the common input, in a bipolar configuration for the detection and for delivering the stimulation pulse, and detects all signal received or sensed at each of electrodes 6 and 7 indifferently and, conversely, stimulates simultaneously and in an identical manner the two atria RA and LA. Such an atrial circuit 24 is well known in the art and may be of any type. The ventricular electrode 3 is connected to a ventricular circuit 23 for the sensing and stimulation of the ventricle, in a conventional manner well known in the art. Electrode 3 is preferably a conventional bipolar endocardial lead.

Such atrial circuits 24 and ventricular circuits 23 are known which can be separately and independently configured to sense cardiac activity in a bipolar mode or in a monopolar (unipolar) mode, the latter referencing one of the two bipolar terminals to the pacemaker case (relative ground). Suitable triple chamber cardiac pacemakers can be obtained by a modification of double chamber pacemakers such as those sold under the model name CHORUS II and CHORUS RM, available from ELA Medical of Montrouge France, and such that a double atrial electrode comprises two unipolar electrodes for implantation of one distal terminal in the left atrium and the other distal terminal in the right atrium and the Y connector. These CHORUS model pacemakers, similar to other double chamber pacemakers, include a microprocessor (25, FIG. 1) and ROM 26 containing software instructions suitable for executing a DDT mode (and perhaps other modes) of pacing and the signal discrimination as described herein. The construction and programming of a software routine, and fixing of the program in a ROM 26 (or other memory device), to implement the triple chamber operation of the present invention are believed to be within the ordinary skill of the art.

Figure 2:
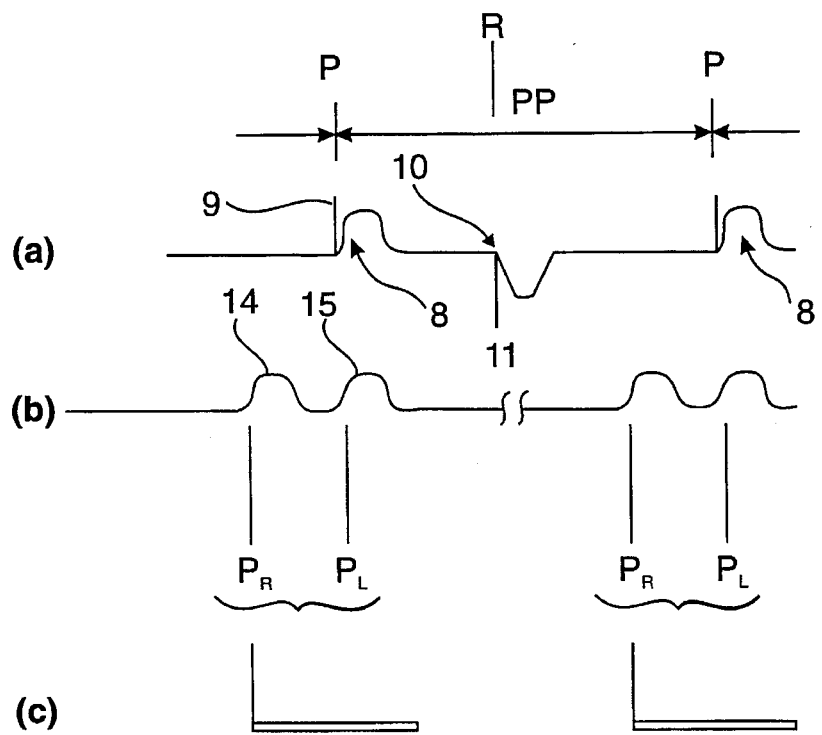
FIGS. 2(a) and 2(b) illustrate the succession over time of the various depolarization waves received by the atrial circuit of the pacemaker of FIG. 1.
FIG. 2(c) illustrates a masking refractory period, illustrating the signal discriminative principles of the present invention.

The signal sensed by atrial circuit 24 follows generally the illustrated waveform shown in FIG. 2(a), and comprises a succession of sensed atrial events 8 (P waves), such that the sensing of a P wave 8, releases immediately an atrial stimulation, corresponding to the pulse peak 9 (FIG. 2(a)). Consequently, both atria are simultaneously stimulated.

The atrial circuit 24 then senses the following ventricular depolarization wave 10 (an R wave) associated with the ventricle stimulation pulse peak 11 delivered to the right ventricle RV by the ventricular electrode 3. The temporal gap between the P wave and the following R wave corresponds to the atrium-ventricle conduction delay (schematized by the dashed arrow 12 on the FIG. 1). Of course, in case of a atrio-ventricular block or an anomaly of the same type, the ventricular circuit 23 of the pacemaker releases automatically the stimulation pulse if no ventricular R wave 10 is detected prior to the end of a predetermined AV delay interval.

In the particular case of the triple chamber stimulation, an atrial depolarization wave 8 can appear, in the absence of stimulation, in the manner illustrated in the larger scale of FIG. 2(b), namely in the form of a wave doublet 14, 15. In the wave doublet, wave 14 corresponds to the P wave $P_R$ of the right atrium RA and wave 15 corresponds to the P wave $P_L$ of the left atrium LA. The spacing between the two waves 14 and 15 depends on the inter-atrial delay (schematized as dashed arrow 16 in FIG. 1). The inter-atrial delay is variable according to each individual and, for each person, increases with the effort (activity level) of the patient.

Furthermore, the pacemaker of the present invention has a fallback mode of functioning, susceptible to initial desynchronization of the ventricular stimulation, for example, by periodically lengthening of the ventricular escape interval until there is a diminution of the rhythm of this stimulation to a base frequency that is bearable, i.e., physiologically tolerable, by the individual. The base frequency can be one that is predetermined by the pacemaker, e.g., a programmed value selected for the patient, or enslaved to a signal coming from a sensor of physiological activities, i.e., a rate responsive determined frequency based on metabolic demand or cardiac output requirements as determined by monitoring some physiological parameter. Such parameters are well known and rate responsive fallback modes implemented in commercial devices such as the models CHORUS RM and OPUS G, available from ELA Medical.

The resynchronization or fallup mode intervenes later, in a progressive manner, when the atrial frequency falls below the maximal synchronization limit. The fallback and fallup modes of functioning, in its various embodiments, are well known in the art, for example, as described in FR-A-2,544, 989, and U.S. Pat. Nos. 5,226,415 and 4,932,406 and therefore will not be described here in more detail.

In the particular case of a triple chamber pacemaker, the signal sensed by the atrial circuit can appear, as indicated above, in the form of a doublet, such as is illustrated in FIG. 2(b). When the "coupling" (namely the inverse of the time period separating the two signals of the doublet) between the two components of the doublet is small (corresponding to typically a period on the order of 200 ms) this means that the same atrial depolarization might be detected twice, once at each atrium. Such a small coupling has as a consequence a risk that the pacemaker will interpret the two successive detections 14, 15, not as a doublet associated with the same atrial depolarization wave, but rather as two successive atrial depolarization waves. This interpretation would cause the pacemaker logic, e.g., microprocessor 25 executing software instructions stored in ROM 26, to believe that there is a high atrial frequency and thereby prolong the fallback mode. In this regard, an interval of 200 ms corresponds to a rhythm of 300 min$^{-1}$.

To remedy this situation, according to a first embodiment of the invention, on each reception of an atrial detection signal, a sufficiently long refractory period (for example of a duration of 200 ms) is used to mask the inter-atrial propagation time. This refractory period, which is illustrated in FIG. 2(c), is a specific period, that can be implemented in a known manner by appropriate programming of a microprocessor of the pacemaker, or by dedicated circuits using an interval clock counter and flip-flops (i.e., a suitable hardwired logic circuit).

In this first embodiment, if the first sensed wave front that has triggered the refractory period is the front of an atrial depolarization directly sensed on the right atrium (that is to say $P_R$ wave 14 as illustrated in FIG. 2(b)), the specific refractory period will be sufficiently long to mask the second wave 15 corresponding to the same depolarization wave that is sensed on the left atrium, namely $P_L$, with a delay period corresponding to the inter-atrial propagation period.

Thus, by application of the present invention, one avoids a false interpretation of the doublet 14, 15 and, an incorrect maintenance of ventricular desynchronization in the fallback mode. The specific refractory period is preferably selected so that it is sufficiently short not to mask the reception of the next atrial depolarization wave.

The interval between two atrial signals sensed by the pacemaker will thus correspond with greater certainty, to the real atrial rhythm. As a result, the logic of the pacemaker will be able thus to determine, with high confidence and in the usual manner, whether to maintain the fallback mode or, on the contrary, to switch to a fallup mode to resynchronize gradually the ventricular stimulation on the atrial rhythm.

In an alternative second embodiment of the invention, the sensing of the wave doublet is masked by switching the atrial detection stage from a bipolar detection mode to a unipolar detection mode when the device is in a fallback mode. In this embodiment, one of the atrial electrodes is connected to the case of the pacemaker and the other to one of the atria (for example, the right atrium). The pacemaker case is referenced to ground. In this configuration, a doublet cannot be sensed, and one thus avoids confusion between atrial depolarization signals that would otherwise be sensed at the atria. Then, when the atrial rate falls below the maximal synchronization frequency, and a fallup mode is initiated, the pacer logic will switch the atrial detection mode back to the bipolar detection mode. In as much as the fallback mode occurs during a fast spontaneous atrial rhythm, typically there is no stimulation of the atrium and thus the monopolar double atrial electrode configuration is of no consequence.

One skilled in that art will appreciate that the present invention can be practiced by other than the described embodiments, which are presented for purposes of illustration and not of limitation.

We claim:

1. A process for controlling a double atrial triple chamber cardiac pacemaker having a bipolar atrial electrode including a right atrial electrode terminal adapted to be coupled to the right atrium and a left atrial electrode terminal adapted to be coupled to the left atrium, the right and left atrial electrode terminals being connected to a single input of an atrial circuit for the detection of atrial events and the stimulation of the atria, and a ventricular electrode connected to a ventricular circuit for the detection of ventricular events and the stimulation of the ventricle, the pacemaker having a fallback mode of cardiac stimulation in which the ventricular stimulation is desynchronized from the atrial rhythm and a fallup mode of cardiac stimulation in which the ventricular stimulation is progressively resynchronized with the atrial rhythm, the process comprising the steps of:

a) sensing at the input of the atrial circuit a succession of signals corresponding to atrial events;

b) in response to a detection of a first signal from said succession of signals at the atrial circuit, establishing an inter-atrial propagation masking period for not sensing atrial events;

c) applying the masking period and measuring an interval of time separating the first signal and sensing of a second signal, the second signal being sensed subsequent to the first signal and said masking period;

d) comparing the measured time interval to a predetermined control value; and e) triggering the fallup mode of progressive re-synchronization in response to the measured time interval becoming greater than the control value.

2. The process of claim 1, wherein step (b) further comprises starting a specific refractory period in response to the detection of the first signal.

3. The process of claim 1 in which the pacemaker has a case referenced to ground, the atrial circuit has a bipolar detection mode and a unipolar detection mode at the input, and a switch to change the atrial circuit between detecting atrial events in a bipolar mode and a monopolar mode, wherein step (b) further comprises changing the atrial circuit from a bipolar mode to a monopolar mode for the detection of atrial signals, and wherein step (e) further comprises, after triggering a fallup mode, switching the atrial circuit from a monopolar mode to a bipolar mode for the detection of atrial events.

4. An apparatus for controlling a double atrial triple chamber cardiac pacemaker comprising:

an atrial circuit to detect atrial events and to stimulate at least one of the left atrium and the right atrium;

an atrial electrode having a right atrial electrode terminal adapted to be coupled to the right atrium and a left atrial electrode terminal adapted to be coupled to the left atrium, the right and left atrial electrode terminals being operatively connected to the atrial circuit;

a ventricular circuit to detect ventricular events and to stimulate a ventricle;

a ventricular electrode adapted to be operatively connected to the ventricle and operatively connected to the ventricular circuit;

a pacing control logic circuit having a fallback mode of cardiac stimulation in which a ventricular stimulation is desynchronized from an atrial rhythm detected by the atrial circuit, and a fallup mode of cardiac stimulation in which the ventricular stimulation is progressively resynchronized with the detected atrial rhythm; and means for changing the pacing control circuit from operation in the fallback mode to operation in the fallup mode, said means being operated to sense successive atrial events at the atrial circuit input;

establish a masking time period corresponding to an inter-atrial propagation interval in response to a detected atrial event for not sensing atrial events;

measure a time interval between a first sensed atrial event and a second sensed atrial event, the second sensed atrial event being sensed subsequent to the first sensed atrial event and the masking time period;

compare the measured time interval to a control value; and initiate the fallup mode in response to the measured time interval becoming greater than the control value.

5. The apparatus of claim 4 wherein the masking time period further comprises a specific refractory period initiated in response to each sensed atrial event.

6. The apparatus of claim 4 further comprising a pacemaker case referenced to a ground, and a switch to change to atrial circuit between a first configuration to detect atrial events in a bipolar mode and second configuration to detect atrial events in a monopolar mode, wherein said changing means is operated to change the atrial circuit from a bipolar mode to a monopolar mode to detect of atrial signals in response to a detection of an atrial event during the fallback mode of operation, and the changing means is operated to switch the atrial circuit from a monopolar mode to a bipolar mode to detect atrial events after initiating the fallup mode of operation.

* * * * *